United States Patent [19]
Tumlinson, III et al.

[11] Patent Number: 6,054,483
[45] Date of Patent: Apr. 25, 2000

[54] PLANT VOLATILE ELICITOR FROM INSECTS

[75] Inventors: James H. Tumlinson, III; Hans T. Alborn, both of Gainesville, Fla.; John H. Loughrin, Versailles, Ky.; Theodoor C. J. Turlings, Neuchatel, Switzerland; Tappey H. Jones, Lexington, Va.

[73] Assignees: The United States of America as represented by the Secretary of Agriculture, Washington, D.C.; Virginia Military Institute Research Laboratories, Inc., Lexington, Va.

[21] Appl. No.: 08/757,701

[22] Filed: Dec. 3, 1996

[51] Int. Cl.$^7$ .......................... A01N 37/44; A01N 37/46; A01N 37/06; C07C 233/46
[52] U.S. Cl. .......................... 514/563; 514/562; 514/561; 514/567; 514/568; 514/572; 562/598; 504/320; 554/35; 554/51; 554/56; 554/58; 554/59; 554/61; 554/63; 554/68; 554/69
[58] Field of Search ..................... 514/561–563, 514/567, 568, 572; 562/598; 504/320; 554/35, 51, 56, 58, 59, 61, 63, 68, 69

[56] References Cited

U.S. PATENT DOCUMENTS

| | | | |
|---|---|---|---|
| 3,947,589 | 3/1976 | Misato et al. | 514/563 |
| 4,240,823 | 12/1980 | Clapot et al. | 504/171 |
| 5,436,226 | 7/1995 | Lulai et al. | 504/291 |
| 5,559,092 | 9/1996 | Gibson et al. | 514/2 |

FOREIGN PATENT DOCUMENTS

| | | |
|---|---|---|
| 3206009 | 9/1991 | Japan . |
| 6157284 | 6/1994 | Japan . |
| 6305906 | 11/1994 | Japan . |
| 9014429 | 11/1990 | WIPO . |

OTHER PUBLICATIONS

Borman, "Attacked Corn Plants Call Wasps to the Rescue", *C&EN*, Sep. 7, 1992.
Farmer et al., *Trends in Cell Biology* 2: 236–241 (1992).
Blechert et al., *Proc. Natl. Acad. Sci.* 92: 4099–4105 (1995).
Turlings et al., *J. Chem. Ecol.* 17(11): 2235–2251 (1991).
Turlings et al., *Florida Entomologist* 74(1): 42–50 (1991).
Turlings et al., *Science* 250:1251–1253 (1990).
Turlings et al., *J. Chem. Ecol.* 16(5): 1577–1589 (1990).
Turlings et al., *Proc. Natl. Acad. Sci.* 89:8399–8402 (1992).
Tumlinson, *Phytoparasitica* 19(4): 341 (1991).
Petitt et al., *J. Insect Behavior*, 5(5): 623–634 (1992).
Kramell et al., *Tetrahedr.* 44:5791–5807 (1988).
Schneider et al., *J. Chrom.* 483: 459–462 (1989).
Bostock et al., *Science* 212(3): 67–69 (1981).
Choi et al., *Plant Physiol.* 104: 1237–1244 (1994).
Castoria et al., *Physiol. Mol. Plant Path.* 41: 127–137 (1992).
Ricker et al., *Physiol. Mol. Plant Path.* 41: 61–72 (1992).
Ricker et al., Physiol. Mol. Plant Path. 44: 65–80 (1994).
Bostock et al., *Plant Physiol.* 100: 1448–1456 (1992).
Turlings et al., *Entomol. Exp. Appl.* 58: 75–82 (1991).
Zidack et al., *Biological Control* 2: 111–117 (1992).
DeAngelis et al., *Environ. Entomol.* 12: 522–527 (1983).
Chemical Abstracts 118 : 58485h (Feb. 1993).

*Primary Examiner*—John Pak
*Attorney, Agent, or Firm*—M. Howard Silverstein; John D. Fado; G. Byron Stover

[57] ABSTRACT

The invention relates to fatty acids conjugated to amino acids and their derivatives that elicit the production and/or release of plant volatiles compounds which attract and/or retain beneficial insects and deter herbivorous insect feeding. These conjugates also induce plants to increase production of pharmacologically important compounds such as taxol, increase fragrance of flowers, and increase production of plant essential oil. The invention also relates to methods for isolating the compounds from herbivorous insect oral secretions and to chemically synthesizing the compounds and their active derivatives.

2 Claims, 8 Drawing Sheets

PLANT VOLATILE ELICITOR FROM INSECTS

BACKGROUND OF THE INVENTION

1. Field of the Invention

This invention relates to compounds which are isolated from the oral secretions of beet armyworm caterpillars, to chemically synthesized compounds, and derivatives thereof. These compounds induce plants to produce and/or release a blend of volatile compounds which, for example, can attract and/or retain beneficial insects, increase fragrance in flowers, increase essential oils in plants, such as mint, which are grown for agricultural production, increase production of pharmacologically important compounds such as taxol, etc, in plants. The present invention also relates to methods for making the compounds and to their use as effective inducers of useful plant compounds.

2. Description of the Related Art

Arthropod plant pests cause extensive and severe damage to major agricultural commodities, both in the field and in the greenhouse environment. In addition to feeding damage, many of these insects also transmit viral diseases. Chemical insecticides are used to control insects that damage agricultural commodities such as corn, cotton, barley, beans, citrus, etc. However, recent concerns about insecticide residues on commodities, resistance of insects to chemical insecticides, hazardous exposure to people who apply pesticides, environmental contamination, destruction of natural biocontrol agents such as beneficial insects, and lack of newly developed insecticides have increased the need for alternative control methods. Furthermore, as pests become more resistant to pesticides, more frequent treatments are required which compounds the problems identified above. An alternative to chemical pesticides is the use of biocontrol agents such as beneficial insects which parasitize and/or eat harmful insects. A useful way to attract and/or keep beneficial insects on crops is needed in order to control harmful herbivorous insects and to at least reduce the amount of pesticides needed for the control of herbivores.

Stress-induced reactions in plants are common and the production and transport of chemicals in response to such stress are proposed to function as a direct defense against herbivores and pathogens. For example, terpenoids and indole are likely to be defensive compounds or by-products of stress-produced compounds. However, in addition to initiating direct chemical defenses, herbivore-injured plants benefit directly by signaling information into their environment. This phenomenon appears to be common; several of the terpenoids released by damaged corn seedlings are also released by leaves of other plants under attack by caterpillars or mites. The chemical signals, in addition to being attractants to natural enemies of the herbivores, may also function as repellents to herbivores. Plants contain a number of organic chemicals which attract pollinating insects or symbiotic organisms and provide self-defense against pathogens and herbivores (Blechert et al, Proc. Natl. Sci, USA, Volume 92, 4099–4105, May, 1995). Wound damage to the leaves of plants from a number of families results in the synthesis of proteinase inhibitor proteins at the wound sites as well as in distal leaves. Jasmonic acid and methyl jasmonate are examples of two plant-derived chemicals which can regulate the expression of wound-inducible proteinase inhibitor genes. Farmer and Ryan (Plant Cell, Volume 4, 129–134, 1992; Trends Cell Biol., Volume 2, 236–241, 1992; both herein incorporated by reference) show that the signal involved in the induction of the high molecular weight proteins involves a lipid-based transduction system which yields jasmonic acid and its methyl ester. It is believed that plant wounding by insects or microbial pathogen attack leads to an interaction of elicitors with receptors thus initiating the octadecanoic-based pathway from $C_{18}$ fatty acid linolenic acid to jasmonic acid. Synthetic jasmonic acid also acts as a powerful inducer of de novo defense protein synthesis, simulating a wound response.

Figure 2A:
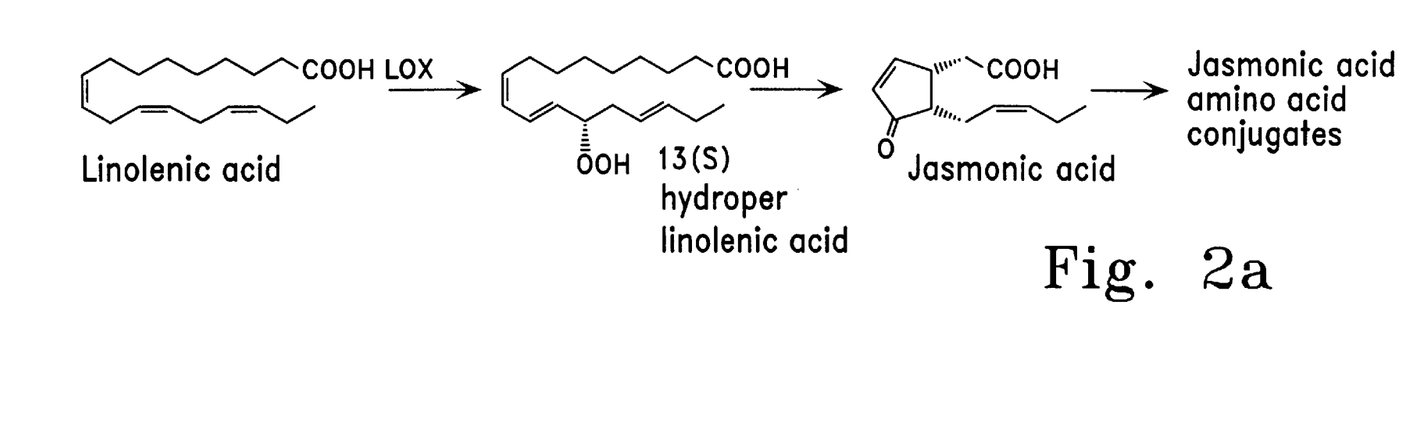
FIG. 2a depicts the octadecanoid pathway found in plants.

Jasmonic acid is a naturally occurring compound identified in plants from at least nine families (Farmer et al, *Trends in Cell Biol.*, supra). Its methyl ester has been used as a perfume fragrance. Jasmonic acid and methyl jasmonate exhibit diverse biological activities in plants in regulating physiological processes and gene expression. Exogenously applied jasmonates have been found to accelerate senescence, induce the synthesis of vegetative storage proteins (VSPs) and proteinase inhibitor proteins in leaves, inhibit pollen germination, stimulate ethylene production in tomato fruit, and promote chlorophyll degradation in barley and anthocyanin production in soybeans. Jasmonates are cyclopentanone compounds (See FIG. 2a) which are commonly present throughout the plant kingdom. The structures and bioactivities of jasmonates are thoroughly reviewed by Hamberg and Gardner (*Biochimica et Biophysica*, Volume 1165, 1–18, 1992) and Parthier (*Biochimica et Biophysica Acta*, Volume 104, 446–454, 1991), the contents of each of which are herein incorporated by reference herein. Jasmonates have been described as exerting a wide range of differing effects on virtually all plants. These effects range from inhibition to promotion of plant processes. As Parthier describes, the effect exhibited on the plant may even be concentration dependent, with some processes stimulated at lower concentrations but inhibited at higher concentrations. Jasmonates have been reported to regulate growth patterns in soybean, induce gene expression during zygote embryogenesis in Brassica, cause tendril coiling in Bryonia and cell-cycle-dependent disruption of microtubles in tobacco cells. Jasmonates have also been shown to inhibit seed germination and seedling growth, stimulate seed germination (at lower concentrations), promote seed dormancy breaking, and promote leaf senescence. Farmer et al (1992, supra) also show that octadecanoid precursors of jasmonic acid; linolenic acid, 13(s)-hydroperoxylinolenic acid and phytodienoic acid can also act as signals for proteinase inhibitor induction in tomato leaves when applied to leaf surfaces. Tazaki (Japanese kokai 2-92220 (A), published Apr. 3, 1990, patent application no. 63-242432, filed Sep. 29, 1988), Yoshihara et al, *Agric. Biol. Chem.*, Volume 53, 2835–2837, 1989), Matsuki et al (*Biosci, Biotech, Biochem.*, Volume 56, 1329–1330, 1992) and Koda et al (*Plant Cell Physiol.*, Volume 29, 969–974, 1988) all disclose treating potato stem fragments with jasmonates in culture to induce tuber formation. These compounds are considered to be endogenous regulators of plant responses.

Corn plants attacked by caterpillars release volatile terpenoids. The parasitic wasp *Cotesia marginiventris*, a generalist larval parasitoid that attacks many different lepidopterous species, locates caterpillar hosts in response to terpenoid release. In locating the caterpillar, the wasp injects an egg into it. In response the caterpillar immediately slows its feeding habit. Later, the wasp egg develops into a larvae that feeds internally on the caterpillar. Tumlinson et al (*C&EN*, Sep. 7, 1992) show that the oral secretions from caterpillars, which contain a combination of digestive fluids and saliva, induce local terpenoid release when applied to scratched surfaces of leaves on corn plant seedlings. The plant response cannot be induced by artificial damage unless the damaged sites are treated with the regurgitant of larvae (*Florida Entomologist*, Volume 74(1), 42–50, March, 1991). The terpenoids are released from the scratched leaves as well as from undamaged leaves. This indicates that the release of terpenoids is systemic and not just localized to the damaged leaves. Undamaged plants are far less attractive to beneficial insects than plants damaged overnight by beet armyworm (BAW, *Spodoptera exigua* Hübner) larvae. The strongest attraction is observed when larvae are put back on an already damaged corn seedling. Furthermore, the corn seedlings on release of the terpenoids and indole become less palatable to the BAW larvae.

While it is known that oral secretions from herbivores and plant-derived precursors of jasmonic acid induce the release of terpenoids by plants, other factors, especially herbivore-derived, have not been identified, isolated, and/or synthesized. Currently, the compounds of the present invention are only available by using crude preparations of oral secretions of herbivorous insects. It is desirable to be able to chemically synthesize these compounds and active derivatives in order to make their use economically feasible. The only substance from insect oral secretions found to induce volatile chemical release by plants thus far is beta-glycosidase from *Peris brassicae* larvae(Mattiacci et al, *PNAS*, USA, Volume 92, 2036, 1995). The present invention provides non-enzymatic herbivore-derived compounds, synthetic compounds and derivatives, different from related art compounds. The compounds of the invention induce plants to produce and/or emit volatile compounds, such as for example, compounds which attract natural enemies of herbivores, increase production of pharmacologically important compounds, increase fragrance of flowers, increase production of plant essential oils, etc.

SUMMARY OF THE INVENTION

It is therefore an object of the present invention to provide novel elicitors and their derivatives of plant volatile terpenoids and indole.

Another object of the present invention is to provide methods for obtaining the elicitors and their derivatives either by synthesis or extraction from oral secretions of herbivores.

A still further object of the present invention is to provide a method for treating plants by administering effective amounts of an elicitor or its derivative in order to stimulate volatile compound production and/or release in plants.

Another object of the present invention is to provide a composition comprising a novel elicitor or its derivative in amounts effective to increase the production and/or release of volatile compounds in plants.

Further objects and advantages of the invention will become apparent from the following description.

BRIEF DESCRIPTION OF THE DRAWINGS

FIG. 6 is a graph showing average of four replicates of relative release of volatiles collected under 2 hours from three corn seedlings that had been treated with 15 microliters of regurgitate equivalents/seedling (300 picomole/plant) or 45 microliters of regurgitate equivalents/seedling (900 picomole/plant) of, the L-glutamine derivative of synthetic elicitor (L-syn), the D-glutamine derivative of synthetic elicitor (D-syn), the sodium form of synthetic 17-hydroxylinolenic acid (17 OH), L-glutamine (L-GLN), D-glutamine (D-GLN) and just buffer (CON). The combined amount in nanogram of Caryophyllene, alpha-trans-bergamontene, (E)-beta-farnesene, (E)nerolidol, and (3E,7E)-4, 8, 12-trimethyl-1, 3, 711, tridecatetraene was used to calculate the release relative to that of corn seedlings treated with IS microliters regurgitate (300 picomole/seedling of natural elicitor).

FIG. 8 is a graph showing the relative release of volatiles (four replicates) collected over a period of about 2 hours from three corn seedlings that had been treated with 5, 17, 50, 170 and 500 picomoles/plant of natural elicitor (Natural) and the L-form of synthetic elicitor (Synth), and treated with just buffer (Buffer). The combined amount in nanograms of Caryophyllene, alphatrans-bergamotene, (E)-beta-farnesene, (E)-nerolidol, and (3E,7E)-4, 8, 12-trimethyl-1, 3, 7, 11, tridecatetraene was used to calculate the release relative to that of corn seedlings treated with 15 microliters regurgitate (300 picomoles/seedling of natural elicitor). The same capital letters indicate no significant difference between doses of natural elicitor and the same lower case letters indicate no significant difference between doses of synthetic elicitor (paired t-test, $p<0.05$). At no dose was there a significant difference between natural and synthetic elicitor.

DETAILED DESCRIPTION OF THE INVENTION

Figure 2B:
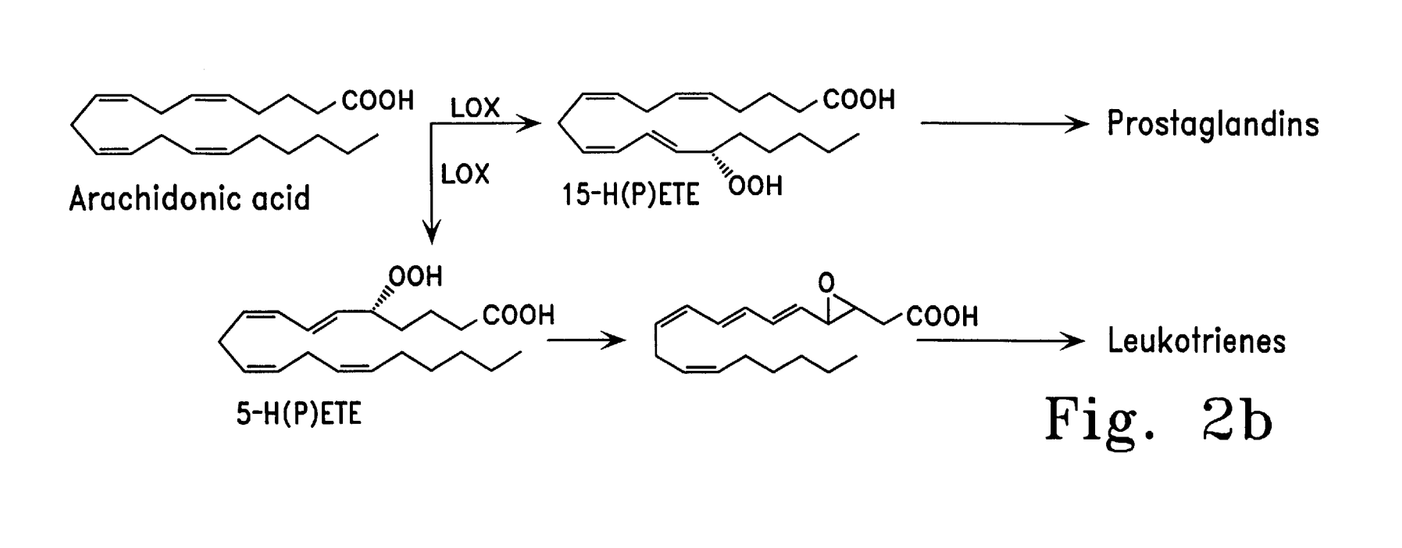
FIG. 2b depicts the synthetic pathway to prostaglandins and leukotrienes.
Figure 3:
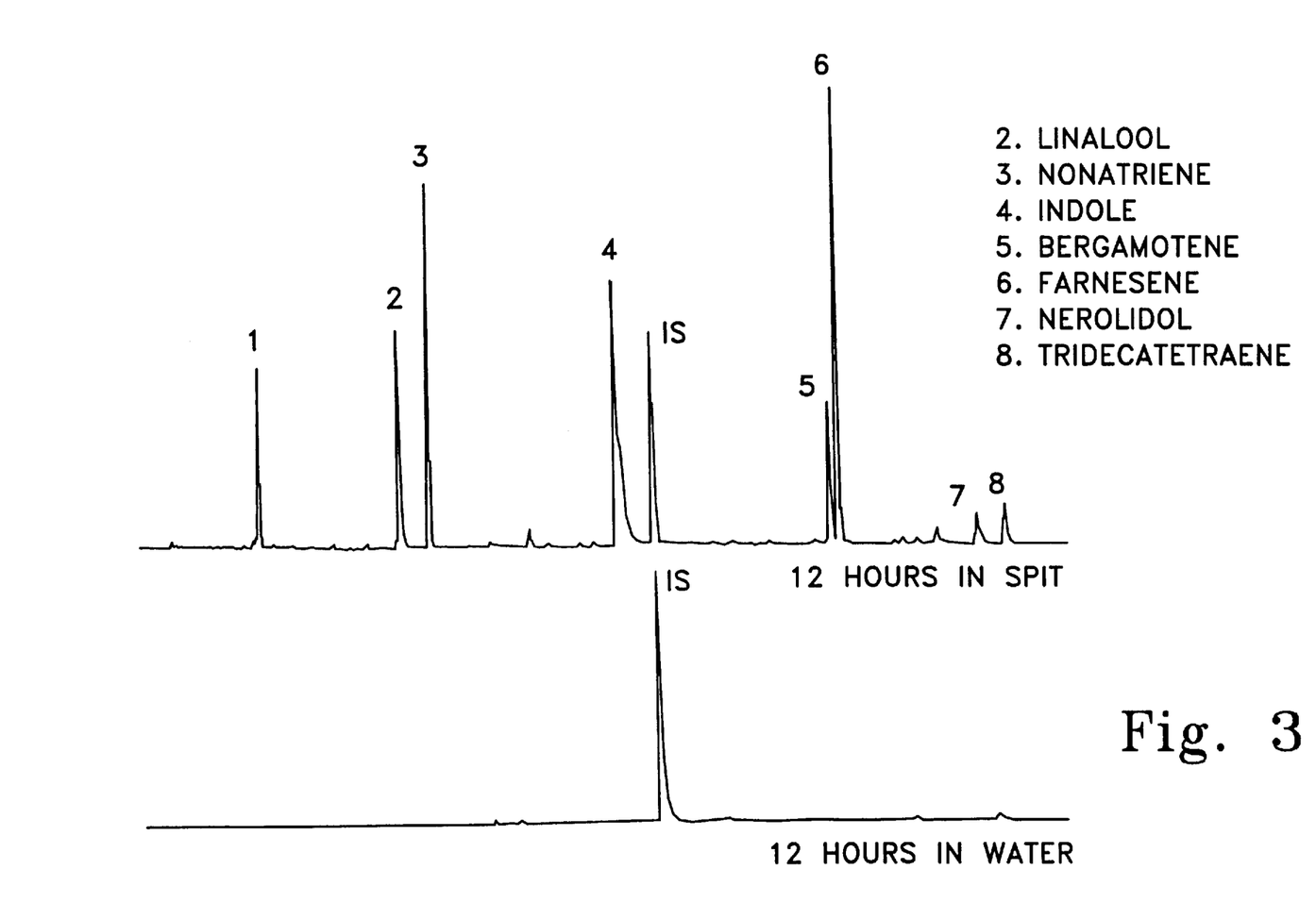
FIG. 3 is a graph showing chromatographic profiles of volatiles released by corn seedlings that were placed for 12 hours in vials with distilled water or vials with a 10-fold dilution of beet armyworm (BAW) regurgitate. The identities of the various compounds have been determined previously (Turlings et al., *J. Chem. Ecology*, Volume 17, 2235–2251, 1991). 1, (Z)-3-hecen-1-yl acetate; 2, linalool; 3, (3E)-4,8-dimethyl-1,3,7-nonatriene; 4, indole; 5,alpha - trans-bergamotene; 6, (E)-beta-farnesene; 7, (E)-nerolidol; and 8, (3E,7E)-4,8,12-trimethyl-1,3,7,11-tridecatetraene. Internal standard (IS) is nonyl acetate (600 ng).

It is found that the defensive reaction of plants, whereby plant volatiles are induced by insect herbivores, is triggered by contact of a substance in the oral secretion of insect herbivores with damaged plant tissues. The isolation, identification and synthesis of a compound from the oral secretion of beet armyworm (*Spodoptera exigua* Hübner) caterpillars that induces corn (*Zea mays* L.) seedlings to release the same blend of volatile compounds as released when they are damaged by caterpillar feeding is the first identification of a non-enzymatic plant volatile elicitor from insects. The production of the compounds of the present invention is not diet related and, thus, does not originate from plants (Turlings et al, *J. Chem. Ecol.*, Volume 19, 411, 1993; herein incorporated by reference in its entirety). The oral secretion of insects fed on an artificial diet is as active as that from those fed on plants. Both corn and cotton respond to BAW damage and to the oral secretions of BAW applied to damaged leaves by producing and releasing terpenoid compounds and indole. While some compounds, like indole, ocimene and farnesene, for example, are released by both plants, other compounds are unique to each plant. This is most likely the result of differences in plant chemistry. Both plants respond systemically to the compounds of the present invention by releasing induced volatiles from undamaged leaves of injured plants (Turlings et al, *PNAS*, USA, Volume 89, 8399, 1992 and Rose et al, *Plant Physio.*, Volume 111, 487, 1996; both herein incorporated by reference in their entirety). These compounds are related to eicosapentaenoic and arachidonic acids from the fungus *Phtophthora infestans* that elicit the production of fungitoxic sesquiterpenes in potato (Bostock et al, *Science*, Volume 212, 67, 1981). These compounds, isolated or synthetic, and active derivatives are related to eicosanoids and prostaglandins that play important regulatory and signaling roles in insects and other animals and the components of the octadecanoid signaling pathway in plants (See FIGS. 2a and 2b). In plant systems studied so far, biosynthesis and release of volatile compounds appear to be induced by jasmonic acid, which is a product of the octadecanoid signaling pathway. Jasmonates have also been reported to stimulate numerous other physiological and defensive processes in plants. Furthermore, the amino acid conjugates of jasmonic acid are involved in physiological and developmental processes in many plants. Therefore, the presence of an elicitor such as an octadecanoate conjugated to an amino acid suggests that the elicitor molecule in some way interacts with or amplifies the octadecanoid pathway in herbivore damaged plants.

Oral secretions from at least five species of lepidopterous larvae and of grasshoppers induce corn seedlings to release the same blend of volatiles (Turlings, 1993, supra). The grasshopper oral secretion appears to be more active than that of caterpillars in inducing corn seedlings to release volatiles.

It has now been discovered that $C_{16}$–$C_{24}$ fatty acids conjugated with an amino acid, whether isolated from the regurgitate of herbivorous insects or chemically synthesized, induce plants to produce and/or release volatile compounds. These released compounds can have many activities, such as for example, attracting and/or retaining beneficial insects on crops and deterring herbivorous insect feeding. The released compounds are, for example, the same compounds released when the plants are damaged by herbivorous insect feeding.

The search for new compounds possessing useful biological activities requires that the new compounds and known compounds, especially natural products and their derivatives, be synthetically prepared. Synthetic preparation of natural compounds allows economical use of these products. The process of the present invention is particularly useful for the manufacture of $C_{16}$–$C_{24}$ fatty acids conjugated with amino acids. The invention describes the preparation of these conjugated compounds which have biological activity in stimulating plants, such as, for example, corn and cotton, to synthesize terpenes and other compounds. The method for synthesizing the specific acid conjugates is important because it allows large quantities of the compounds to be produced in a relatively short period of time as compared to the labor intensive method of extracting the acids from the oral secretions of herbivorous insects.

Figure 1:
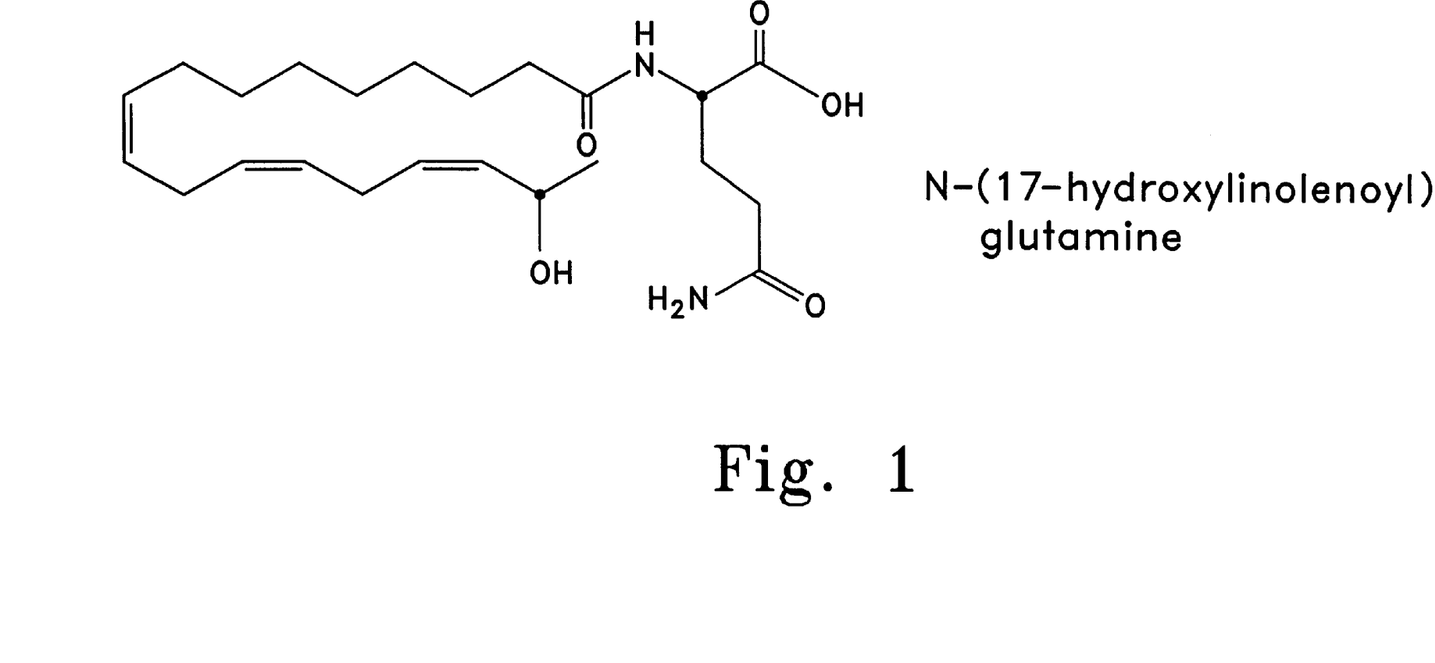
FIG. 1 depicts the structure of N-(17-hydroxylinolenoyl) glutamine.

To isolate and identify the active compound from beet armyworm caterpillar, oral secretions of the caterpillar are centrifuged to remove solid material and the supernatant is filter sterilized. The proteins are precipitated from the supernatant and the precipitate removed by centrifugation. The resulting supernatant is fractionated by reverse phase solid phase extraction using water, acetonitrile in water (about 50/50) and acetonitrile. The resulting aliquots are further separated by liquid chromatography. The collected fractions are bioassayed to identify the fraction(s) containing the active material. The active material is purified by a series of chromatographic steps including reverse phase HPLC and liquid chromatography to obtain the active compound at about 99% purity by HPLC. The purified compound is identified as a 17-hydroxylinolenic acid glutamine conjugate (FIG. 1) The $C_{16}$ to $C_{24}$ fatty acids conjugated with an amino acid refers to a combination of a $C_{16}$ to $C_{24}$ fatty acid and a D- or L-amino acid. The term fatty acid is meant to include $C_{16}$ to $C_{24}$ carboxylic acids. Carboxylic acids, for the purposes of this application, include aliphatic acids and their unsaturated and saturated, alkylated, substituted, oxidized or hydroxylated derivatives. Examples of fatty acids of the present invention include, for example, hexadecanoic acid, octadecanoic acid, eicosanoic acid, tetracosanoic acid, palmitoleic acid, oleic acid, linoleic acid, linolenic acid, arachadonic acid, etc. For the purposes of the present invention, $C_{16}$ to $C_{24}$ acids can be alkylated, substituted, oxidized, or hydroxylated derivatives. Substituents on the aliphatic chain may include aryl groups, amino groups, formyl groups, or other heteroatom groups. The compounds of the present invention include, but are not limited to, 17-hydroxylinolenoyl-L-glutamine, 17-hydroxylinolenoyl-D-glutamine, linolenoyl-L-glutamine, linolenoyl-D-glutamine, and N-(17-hydroxy-linolenoyl)glutamine which is isolated from beet armyworm oral secretions. The most preferred is the unsaturated $C_{18}$ carboxylic acid, 17-hydroxylinolenic acid which is conjugated with L-glutamine.

The term amino acid for the purposes of this invention is meant to include any alpha-amino acid including D- or L-forms. Examples of amino acids useful in the present invention include glutamine, asparagine, alanine, valine, leucine, isoleucine, proline, methionine, phenylalanine, tryptophan, glycine, serine, threonine, cysteine, tyrosine, aspartic acid, glutamic acid, lysine, arginine, histidine, etc. L-glutamine is most preferred. The amino acid is conjugated with the fatty acid via an amide bond with the alpha amino group.

The synthesis of the compounds (FIG. 5) of the invention begins with the production of 1-ethoxyethyloxy-8-benzoyl-3,6-nonadiyne (1) by reacting ethoxyethyl ether of 3,6-heptadiynol with an aldehyde such as acetaldehyde, for example, and benzoyl chloride. Any aldehyde can be used that will result in a fatty acid as defined by the present application. Known compounds, such as for example, ethoxyethyl ether of 3,6-heptadiynol, acetaldehyde, and benzoyl chloride can be purchased or prepared by any known method in the art. The ethoxyethyl ether group is removed from compound I to form 3,6-nonadiyn-1,8-diol, 8 benzoate which is reacted with quinoline and Lindlar catalyst to form 8-benzoyl-Z,Z-3,6-nonadiene-1-ol (II). Compound II is sulfonated and then iodinated. The mixture is then treated with triphenylphosphine to form 1triphenylphosphonium-8-benzoyloxy-Z,Z-3,6-nonadiene iodide (III). Compound III is reacted with hexamethyldisilazide to form the corresponding ylide. The ylide is reacted with a $CHO(CH_2)_nCOOCH_3$, wherein n=about 5–13, to form methyl 17-benzoyloxymethyllinolenate (IV). The benzoyl group is then removed to obtain a hydroxy fatty acid. The fatty acid can be hydrogenated to obtain a saturated compound using methods standard in the art. The amino group is then conjugated to the fatty acid via an amide bond with the alpha amino group.

More specifically, to chemically prepare the compounds of the invention, the $C_{16}$–$C_{24}$ fatty acids are prepared first, and isolated. The isolated fatty acid is then conjugated to the amino acid. The first step of the process produces a 1-ethoxyethyloxy-8-benzoyl-3,6nonadiyne [I] by reacting ethoxyethyl ether of 3,6 heptadiynol in an anhydrous ethereal solvent, such as, for example, tetrahydrofuran with an organometallic base, such as, for example, ethylmagnesiumbromide in an anhydrous ethereal solvent, tetrahydrofuran, for example, at about 0° C. Approximately 1 ml of acetaldehyde, or any other aldehyde, is added to the mixture. The mixture is then treated with an anhydrous tertiary amine base, such as for example, pyridine, followed by benzoyl chloride to acylate the resulting alcohol. This mixture is stirred for approximately 1 hour and is then treated with a saturated ammonium chloride and extracted into a non-polar solvent, such as, for example, diethyl ether. The organic phase is separated, washed in brine and dried over anhydrous inorganic salt, such as, for example, $MgSO_4$. For the purposes of this application, brine is defined as a saturated sodium chloride solution. The dried preparation containing I is reconstituted in an alcohol solvent, such as, for example, methanol and treated with an organic acid, such as for example, p-toluenesulfonic acid to remove the ethoxyethyl ether group. This is allowed to react until almost no starting materials remain. The mixture is treated with a mild inorganic base, such as for example, $NaHCO_3$, and the solvent is removed in vacuo. The residue is taken up in a non-polar solvent, such as for example, diethyl ether and purified by liquid chromatography over silica gel to obtain 3,6-nonadiyne-1,8-diol, 8-benzoate. The solvent is removed in vacuo and the residue taken up in an alcoholic solvent, such as, for example, ethanol, containing quinoline and Lindlar catalyst and stirred at about room temperature until hydrogen uptake ceases. The product is isolated by liquid chromatography through celite and the solvent removed in vacuo. The residue is taken up in a non-polar solvent, such as, for example, diethyl ether, washed with dilute aqueous acid, such as, for example, 10% HCL, and dried over an anhydrous inorganic salt, such as, for example, $MgSO_4$. The dried residue is taken up in methylene chloride and this contains compound II.

1-Triphenylphosphonium-8-benzoyloxy-Z,Z-3,6-nonadiene, iodide [III] is produced by reacting the methylene chloride preparation containing II with a tertiary amine, such as, for example, triethyl amine and a sulfonyl chloride, such as, for example, methanesulfonylchloride to produce the corresponding sulfonate. This is then taken up in a non-polar solvent, such as, for example, diethyl ether, washed, dried and solvent removed in vacuo. The residue is taken up in a low molecular weight ketonic solvent such as acetone and stirred with an excess of sodium iodide for approximately 2–6 hours. The solvent is removed in vacuo, and the residue taken up in a non-polar solvent such as diethyl ether and washed with a dilute solution of sodium thiosulfate and dried over an anhydrous inorganic salt such as $MgSO_4$ For the purposes of this application, a dilute solution of sodium thiosulfate includes solutions of about 5–20% sodium thiosulfate. The solvent is removed in vacuo and the residue is taken up in acetonitrile and treated with triphenylphosphine and refluxed for at least about 8–12 hours. The solvent is removed and the brittle foam is taken up in a polar ethereal solvent, such as for example, tetrahydrofuran and cooled to approximately -80° C. under an argon atmosphere. This contains compound III.

The mixture containing III is then treated with sodium hexamethyldisilazide in order to form the corresponding ylide and then a solution of $CHO(CH_2)_nCOOCH_3$ in a polar ethereal solvent, such as for example, tetrahydrofuran is added and the mixture is stirred for at least about 8–12 hours and warmed to approximately room temperature. For the purposes of this invention n=about 5–13. Compound IV is extracted from this mixture by the addition of a saturated ammonium chloride solution and a non-polar solvent such as diethyl ether. The organic phase is removed and contains Methyl, 17-benzoyloxy($CHO(CH_2)_nCOOCH_3$) which is compound IV.

The benzoyl group and the methoxy group are removed by treating the mixture containing IV with aqueous LiOH, and tetrahydrofuran at about room temperature for at least about 8 hours in order to obtain a hydroxy fatty acid [V]. The compound is extracted using standard methods in the art. A saturated product can be obtained by hydrogenating compound V using methods standard in the art.

To obtain the amino acid conjugate, compound V is reacted with the lithium salt of the desired L- or D-amino acid. The lithium salt of the amino acid is dispersed in an aprotic polar solvent such as for example DMF to which is added water and freshly distilled triethylamine. In a second container compound V is dissolved in an aprotic polar solvent, such as for example DMF, followed by hydroxybenzotriazole. 1-ethyl-3 (Dimethylaminopropyl) carbodiimide is added and the solution stirred for about 1 minute and then the contents of the container containing the amino acid is added and stirred overnight at about room temperature to couple the two compounds. The conjugate is extracted and purified by column chromatography using methods well established in the prior art.

The compounds of the present invention can be sprayed on crop plants in the field under conditions which induce plants to produce and/or release volatile chemicals in order to attract beneficial insects which are natural enemies of the herbivorous pests. The compounds are sprayed on crop plants when an outbreak of insect pests is first detected to recruit beneficial insects earlier and in larger numbers than occurs under natural conditions. In addition, "factory" reared parasitic insects or other beneficial insects can be released at the time of spraying in order to retain the released insects in the target area until they find the pest insects. The compounds of the present invention are mixed with a surfactant, such as, for example, Silwet L-77 (polyalkylenoxide modified polydimethylsiloxane; Union Carbide, Tarrytown, N.J.), which ensures that the compound of the present invention is carried into the plant. Silwet L-77 is used to carry many substances into plant leaves including plant hormones like gibberellin and cytokinin (Zidack et al, *Biological Control,* Volume 2, 111–117, 1992; herein incorporated by reference). It reduces the surface tension to about 20 dynes $cm^{-1}$ allowing the liquid to enter leaf stomata.

Timing of spray application is coordinated with day length such that plants would be sprayed in late afternoon to allow overnight incubation so that plants would produce and/or release volatiles during the next photophase. In some instances, depending on the plant species, an incubation period of greater than 24 hours might be required to induce plant volatile production and/or release. For example, in laboratory conditions, soybeans respond more slowly to the application of the compounds of the present invention than do corn seedlings.

Another method of using the compounds of the present invention includes spraying plants with the compounds of the present invention in surfactant solutions, as described above, before the plants are attacked by pests in order to immunize the plants to insect attack. It is well established that systemic acquired resistance occurs in plants wherein they become resistant to subsequent attack after undergoing an initial attack by insects or pathogens. Plants attacked by beet armyworm larvae or treated with beet armyworm larval oral secretions will release volatile compounds from undamaged leaves (Turlings et al, 1992, supra, Rose et al, 1996 supra; both herein incorporated by reference in their entirety). By spraying plants with these compounds the biochemical mechanisms are primed to respond more quickly and strongly if they are subsequently attacked by pests. The plants will not sustain the initial damage as they would if initially attacked by insects.

The elicitor compounds of the present invention can be used to increase the production of essential oils by mint and other crops commercially grown for the production of essential oils. Compounds are mixed with a surfactant, as described above, such as Silwet-77 that will allow the elicitor to penetrate the leaf surface through the stomata.

The elicitor compounds of the present invention can be supplied hydroponically through the roots of plants by adding the elicitors to the hydroponic solutions used to feed plants. Since these compounds have both a polar amino acid group and a non-polar lipid moiety, they are soluble in a wide variety both non-polar and polar solvents, such as, for example, water and organic solvents. By allowing the plants to take the compounds up through the roots they can be induced to produce certain compounds of industrial and medicinal value or to produce increased amounts of certain compounds that will enhance their flavor. Furthermore, the elicitor compounds of the present invention can be added to plant cell cultures or tissue cultures to induce the production of increased amounts of compounds of industrial or medicinal value. For example, an elicitor of the present invention can be added to cell cultures of taxol-producing plants, such as Taxus media, to increase the production of taxol, an important cancer fighting agent.

The elicitor compounds of the present invention can be used to increase the perfume smell of cut flowers and floral arrangements. The compounds can be dissolved in a solution such as approximately 50 mM sodium phosphate/citrate buffer or a similar buffer, and the freshly cut stems of the flowers immersed in a container or vase containing the solution containing the elicitor compounds of the present invention and the flowers take up the solution through the cut stems. Water is added as needed to maintain the flowers in fresh condition. After standing overnight in the solution, flowers will begin to release increased amounts of perfume when they are exposed to light, especially sunlight.

The following examples are intended to further illustrate the invention and are not intended to limit the scope as defined by the claims.

EXAMPLE 1

To isolate N[17-hydroxylinolenoyl]-glutamine (Example 1), oral secretions were collected by gently squeezing 3rd–5th instar BAW caterpillars that had been fed on corn seedlings, causing them to regurgitate. The liquid oral secretion is drawn into a glass capillary tube connected to a small glass bottle under vacuum. The oral secretion is centrifuged at approximately 16,000 g for about 30 minutes to eliminate solid material followed by a sterile filtering of the supernatant through an approximately 0.22 μm membrane filter (Millex GV, Millipore, Bedford, Mass.). An equal amount of approximately 50 mM, about pH 3.3 phosphate buffer is added and precipitated proteins removed by centrifugation. An approximately 0.5 ml aliquot of regurgitate in buffer is fractionated on a reverse phase solid-phase extraction cartridge. The aliquots are put on an activated SPE octadecyl, 6 ml cartridge (Bakerbond, J. T. Baker, Phillipsburg N.J.). A first fraction is collected by allowing about 2 ml of water to flow through the column by gravity flow. Two more fractions are collected by successive elution with about 2 ml of approximately 50% acetonitrile in water (fraction 2) and about 2 ml of about 100% acetonitrile. All fractions are vacuum concentrated to near dryness (Speed Vac rotary concentrator, Savant Instruments, Farmingdale, N.Y.) and redissolved in about 0.5 ml of approximately 50 mM, about pH 8 buffer, prior to being bioassayed in the manner of Turlings et al (*J. Chem. Ecol.,* Volume 19, page 411, 1993; herein incorporated by reference). The total activity of the chromatographed oral secretion elutes from the reverse phase cartridge with the approximately 50% acetonitrile in water indicating a molecule of medium polarity. To bioassay the oral secretion, about 45 μl of BAW regurgitate is concentrated to dryness and dissolved in about 1500 μl of an approximately 50 mM sodium phosphate/citrate buffer about pH 8. The solution is divided into three about 500 μl portions in 1 ml glass vials. At about 9 to 11 pm, a corn plant that had spent at least about 1 hour in darkness is cut above the root with a razor blade and transferred to each vial and allowed to suck up the approximately 500 μl aliquots of crude regurgitate or chromatography fractions for about 12 hours in complete darkness. Three seedlings for each treatment are put together in a volatile collection chamber (Turlings et al, 1991, supra). Purified and humidified air is drawn for about 2 hours through the chamber at about 300 ml/min and through a polymer adsorbent (super q 80/100 Cat. No. 2735, Alltech Associates, Deerfield, Ill.). The adsorbent is removed from the chamber and extracted with about 150 μl methylene chloride and approximately 600 ng of the internal standard nonyl acetate in about 30 μl methylene chloride was added. The extract is analyzed by capillary gas chromatography (Turlings et al, *J. Chem. Ecol.,* Volume 17, 2235, 1991; herein incorporated by reference). The results are shown in FIG. 3.

The active material from solid phase extraction is further fractionated on reverse phase HPLC using a LDC 4100 pump with SM5000 diode array UV detector (LDC Analytical, Riviera Beach, Fla.), monitoring UV detection from about 190–360 nm. The reverse phase column (Waters Nova Pac C 18 4 μ ID×150 mm column, Waters, Milliford, Mass.) is eluted with a solvent gradient from about 0 to 25% acetonitrile in water in about 15 minutes followed by an increase to about 100% acetonitrile in about 15 minutes, using a flow of approximately 1 ml/min. The eluate is collected in about 2 ml fractions. Approximately all the activity is contained in the about 7–9 ml fraction. This fraction is further separated on a second reverse phase HPLC column with different selectivity (YMC 18 ODS-AQ S-5 200 Å, 46 mm ID×250 mm (YMC Co., ltd. Kyoto, Japan) using the same solvent gradient. Almost all the active material elutes in the approximately 20–22 ml fraction. This fraction contains two overlapping peaks which could be separated on the same column using a solvent gradient of approximately 20 to 60% acetonitrile in water over about 20 minutes. This component, with maximum UV adsorption at about 200 nm, eluting from the final column is active and its biological activity is equivalent to that of the original crude regurgitate. When this fraction containing this component is lyophilized, redissolved in about pH 8 phosphate/citrate buffer, and reanalyzed on the final HPLC system (reverse phase HPLC column with different selectivity, supra) the retention volume of the active compound is reduced by about 50%. However, when the pH is adjusted to about 7, the component regained its original retention volume. This strongly indicates that the active compound is a weak acid, which is confirmed by extraction of the active material into $CH_2Cl_2$ from an acidified (approximately pH 3) aqueous solution, but not from an aqueous solution at about pH 8.

An approximately 2 ml aliquot of the active HPLC fraction is concentrated to dryness under vacuum. The sample is redissolved in approximately 2 ml water. Approximately 100 μl acetic acid and approximately 2 ml methylene chloride are added and the mixture shaken for about 5 minutes. The water and organic phase are separated and concentrated to approximately dryness under vacuum. Bioassay of the fractions redissolved in approximately pH 8 buffer show that about all biologically active material to be present in the organic phase and HPLC analysis, as described above, shows the peak to be present in this fraction. Extracting approximately all biological activity from the organic phase back into pH 8 buffer strongly indicates lipid character and an acidic functional group.

About a 0.5 ml aliquot of the methylene chloride fraction is put on an activated 3 ml 10SPE diol cartridge (Bakerbond, J. T. Baker, Phillipsburg, N.J.). The column is rinsed with a first fraction of about 3 ml methylene chloride followed by approximately 2 ml of methanol. The active component elutes from this column with the methanol. Rechromatography of the active component on the final reverse phase HPLC column indicates that it is greater than about 99% pure by HPLC.

Figure 4:
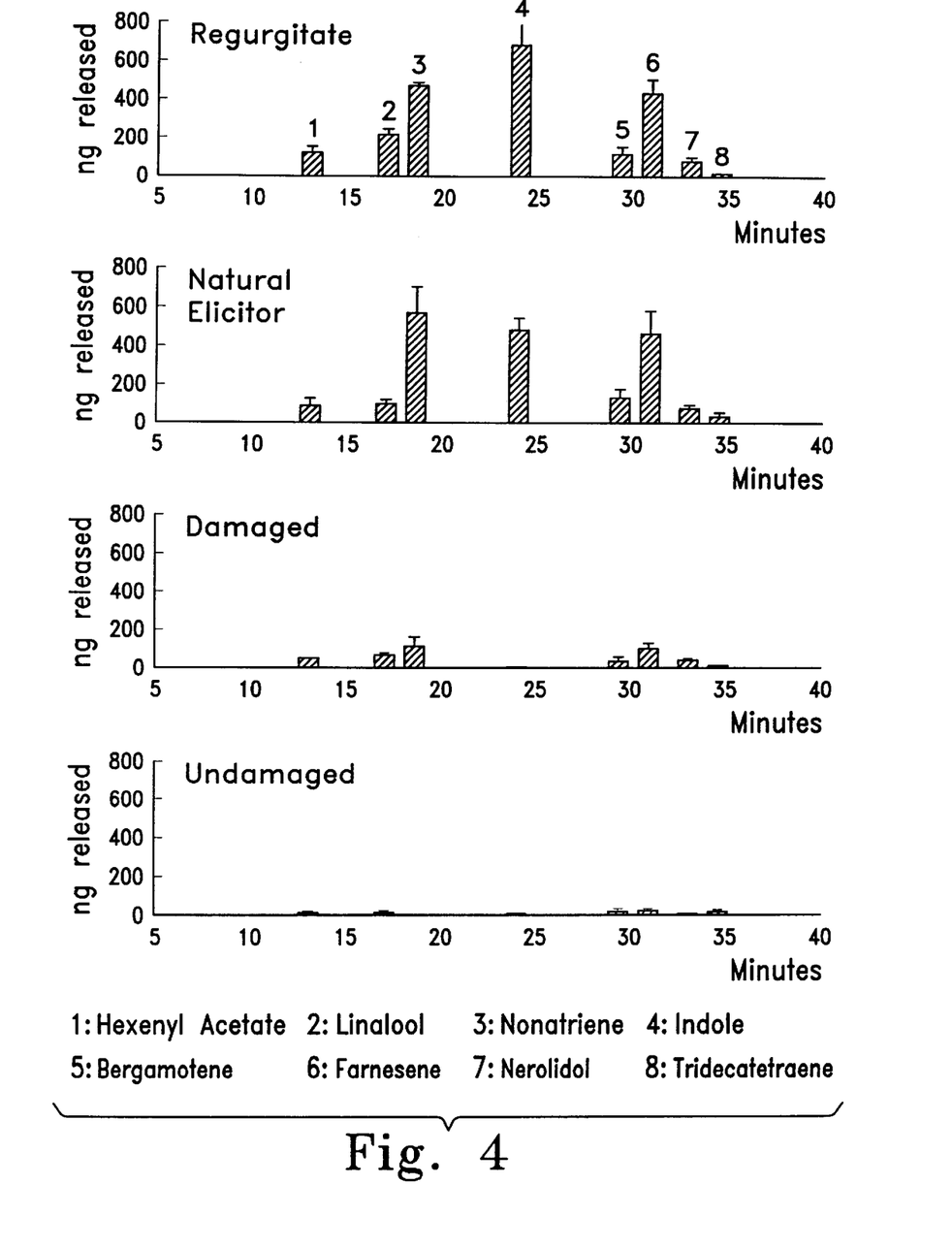
FIG. 4 is a graph showing average amounts (ng/2 hr.) of four replicates of volatiles collected from three corn seedlings that have been treated with either 15 microliters of BAW regurgitate/seedling on the damage site (Regrugitate), 15 microliters regurgitate equivalents of pure natural elicitor (Natural elicitor), or an equal amount of just buffer (Damaged), and undamaged control plants (Undamaged).

The biological activity of the pure component is confirmed by applying it in a buffer solution to artificially damaged leaves on corn plants. This treatment resulted in the same induced production of characteristic volatiles as treatment with BAW regurgitate. The results are shown in FIG. 4. Application of only buffer on an artificially damaged site did not result in release of volatiles.

EXAMPLE 2

The active compound was identified by mass and infrared spectroscopy and by chemical transformations. Up to about 4 μl of active material (up to about 40 ng) in an approximately 50% acetonitrile in water solution and about 1 μl of trifluoroacetic acid is added to a glycerol matrix and analyzed with Fast atom bombardment mass spectroscopy (FAB-MS), on a VG Zagspec (VG Analytical, Fisons Instrument, Manchester, England). To obtain sodium adducts, the TFA is substituted with approximately 1 μl of an approximately 1 M sodium chloride solution. High resolution mass measurements are obtained by adding polyethylene glycol (about 1 μl) with an average mass of about 400 Dalton (PEG 400) to the glycerol matrix to give reference ions of known mass for an exact calibration of the mass scale. Possible elemental compositions are established, allowing a limitation of a maximum of approximately 30 C, a maximum of approximately 8 O, and minimum of approximately 2 O. The number of nitrogens could be either about 2, 4, or 6. The mass window for the calculations was limited to an error of about 10 milli mass units. Daughter ion spectra are obtained from samples in the same FAB matrix as above using a high resolution MS\MS tandem four-sector mass spectrometer (Jeol HX/HX110A, Tokyo, Japan). The nitrogen collision gas is adjusted to give an approximately 60% reduction in intensity of mother ion and the resulting pattern of daughter ion analyzed in a second high resolution mass spectrometer.

The FAB-MS analysis produces diagnostic peaks at m\z 423.280 $(M+H)^+$ in the positive ion mode, and m/z 421.2733 $(M-H)^-$ in the negative ion mode. The addition of sodium chloride to the FAB matrix results in reduced intensity of the m/z 423.280 and the appearance of strong m/z 445.2628 $(M+H)^+$. These results confirm that the active component is a weak acid with a molecular weight of 422.274 Dalton for the neutral molecule in acid form. The $C_{23}H_{38}N_2O_5$ (422.278 Dalton) is the only possible elemental composition.

Daughter ions of the sodium salt, m/z 445, obtained by FAB MS include a dominating ion at m/z 427 (445–18), while daughter ions of M/Z 423 gave a strong 405 (423–18), both indicating a loss of water. The lower mass region shows a characteristic pattern of m/z 147, 130, 129, 101, 84, 67, 56, which resembles the electron impact (EI) mass spectra of both glutamine and glutamic acid, but is more consistent with that of glutamine. (National Institute of Standards and Technology, Gaithersburg, Md., Mass spectral library). Characteristic ions for glutamine are m/Z 130, 129, 101, 84 (base peak) and 56. Subtraction of glutamine, linked via an ester or amide bond, gave $C_{18}H_{30}O_3$, as an elemental composition of the second part of the molecule, which is consistent with a hydroxy C18 acid with three double bonds.

For gas chromatographic-mass spectral (GC/MS) analysis, active material to an equivalent of approximately 100 μl regurgitant is methanolyzed with methanol/acetic acid anhydride following the procedures of J. M. L. Mee, *Biomed. Mass Spectrom.*, Volume 4, 178, 1977, herein incorporated by reference. The sample is concentrated to dryness and approximately 50 μl of dry methanol and approximately 50 μl acetic anhydride is added. In a nitrogen atmosphere, the sample is heated to about 100° C. for about ten minutes and concentrated to dryness by a gentle $N_2$ blowing. Approximately 50 μl methylene chloride is added and the sample is analyzed by GC/MS. A Finnigan TSQ 700 mass spectrometer (Finnigan MAT, San Jose, Calif.) is combined with a HP 5890 gas chromatograph (Hewlet Packard, Palo Alto, Calif.). Helium is used as a carrier gas and methane is used as the reaction gas for chemical ionization. A polar capillary column (OV351, 25 m×0.25 ID, Scandinaviska Genetec, Kungsbacka Sv) is held at about 60° C. for approximately three minutes and then temperature programmed about 10° C./min to about 250° C. and held at that temperature for approximately 18 minutes. Splitless injection occurs at about 225° C.

This reveals two prominent peaks. Chemical ionization (CI)/MS analysis of the first of these peaks with a retention time of approximately 21.05 minutes reveals a prominent $(M+1)^+$ ion at m/z 144 and electron impact (EI)/MS analysis reveals a molecular ion at m/z 143 and diagnostic ions at m/z 84 (base peak), 56, and 41 identifying it as the methyl ester of pyroglutamate, which by congruence in GC retention time and mass spectrum with the product of glutamine treated in the same way confirms the presence of glutamine.

The CI mass spectrum of the second peak (Rt about 27.55 min), contains a very weak m/z 309 (M+1)$^+$ ion and a predominant ion at m/z 291 due to loss of water (M+1–18)$^+$. Loss of methanol gave an ion at m/z 277 (M+1–32)$^+$ and loss of both water and methanol gives an ion at m/z 259 (M+1–18–32)$^+$. The EI spectrum of the same peak shows no molecular ion but a strong n/z 290 due to loss of water (M–18)$^+$, and a fragmentation pattern of ions characteristic for a straight chain unsaturated hydrocarbon. These results are consistent with the methyl ester of a hydroxy acid. A smaller peak in the chromatogram has retention characteristics and a mass spectrum consistent with the acetate of the same hydroxy acid methyl ester.

Fourier transform infrared analysis was performed using a Fourier transform Infrared detector 5965B and 5890 Capillary GC (Hewlet Packard, Palo Alto, Calif.). Nitrogen is used as the carrier gas. A non-polar DB1 column (25 m×0.35 mm ID, J&W Scientific, Folsom, Calif.) was held at approximately 60° C. for about three minutes and then temperature programmed to about 10° C./min to about 250° C. and held at that temperature for approximately 18 minutes. Splitless injection at about 225° C. Hydroxy acid methyl ester, Rt. about 25.38 minutes.

Fourier transform infrared analysis of the hydroxy acid methyl ester peak from GC produces a weak, broad absorption at about 3646 cm$^{-1}$ indicating an alcohol and absorption bands at about 3019, 2935, 2865 cm$^{-1}$, typical for a straight chain non-conjugated unsaturated hydrocarbon. The intensity of the approximately 3019 cm$^{-1}$ peak relative to the others indicates three cis double bonds and the absence of a peak in the area of about 960 to 980 cm$^{-1}$ indicates no trans double bonds are present. An intense absorption at about 1758 cm$^{-1}$ confirms the presence of a methyl ester.

These results all confirm that the molecule consists of two subunits, glutamine and a hydroxy $C_{18}$ acid with three cis bonds. These two components could be attached in three ways to give the right elemental composition. However, only an amide bond between glutamine and the acid moiety of the hydroxy acid would result in a free hydroxy as indicated by the FAB/MS experiments without also giving a free amine for which there is no evidence.

EXAMPLE 3

To determine the positions of the double bonds and the hydroxyl group, the methyl ester of the hydroxy acid is partially saturated following the procedures of Attygalle et al (Tetrahedron Lett., Volume 36, 5471, 1195; herein incorporated by reference). After concentration to dryness, the sample is redissolved in approximately 10 μl ethanol, approximately 30 μl of about 10% hydrazine in ethanol and approximately 30 μl of about 0.6% hydrogen peroxide in ethanol is added, and the solution is heated to about 60° C. for about 1 hour. After being allowed to cool to about room temperature, about 35 μl of approximately 5% HCl in water is added. The solution is extracted approximately twice with approximately 40 μl GC$^2$ hexane and the hexane solution is washed about four times with approximately 50 μl of water before being analyzed by GC/MS as described above in Example 3.

Partial reduction results in a mixture of mono- and di-unsaturated products as established by GC/MS analysis. This mixture is then subject to ozonolysis following the procedures of Beroza et al., *Anal. Chem.*, Volume 38, 1976, 1966 and *Anal. Chem.*, Volume 39, 1131, 1967, both herein incorporated by reference in their entirety. The product is analyzed by GC/MS as described above in Example 3.

GC/MS analysis (CI) shows the presence of three diagnostic GC peaks with (M+1)$^+$ ions at m/z 187, 229 and 271, corresponding to H(CO)(CH$_2$)$_n$(CO)OCH$_3$ with n=7, 10 and 13, respectively. Methyl linolenate treated in the same way gives identical products. Thus, the olefinic bonds in the chain are located on carbons 9, 12 and 15 and the alcohol group on either the 17th or 18th carbon.

EXAMPLE 4

To determine the position of the hydroxyl group, the hydroxy acid methyl ester is dissolved in approximately 50 μl ethyl acetate. About five milligrams of Pd$_2$O is added and total saturation is achieved by a gentle bubbling of H$_2$ for about 18 hours. GC/MS (EI) analysis (as in Example 3 above) of the product shows an m/z 299 (M–15) and strong m/z 270/271 (M–44/M–43) which are conclusive for a hydroxyl group on C17. A pyrrolidide derivative of the saturated methyl ester is prepared following procedures of B.Å. Anderson, Prog. *Chem. Fats and other Lipids*, Volume 16, 279, 1978; which is herein incorporated by reference in its entirety. GC/MS analysis of the product (as in Example 3 above) shows an m/z 338 (M–15) and m/z 309 (M–44) confirming the C17 location of the hydroxyl group.

EXAMPLE 5

The following procedure is used to produce the synthetic 17-hydroxy linolenic acid glutamine conjugate.

Figure 5:
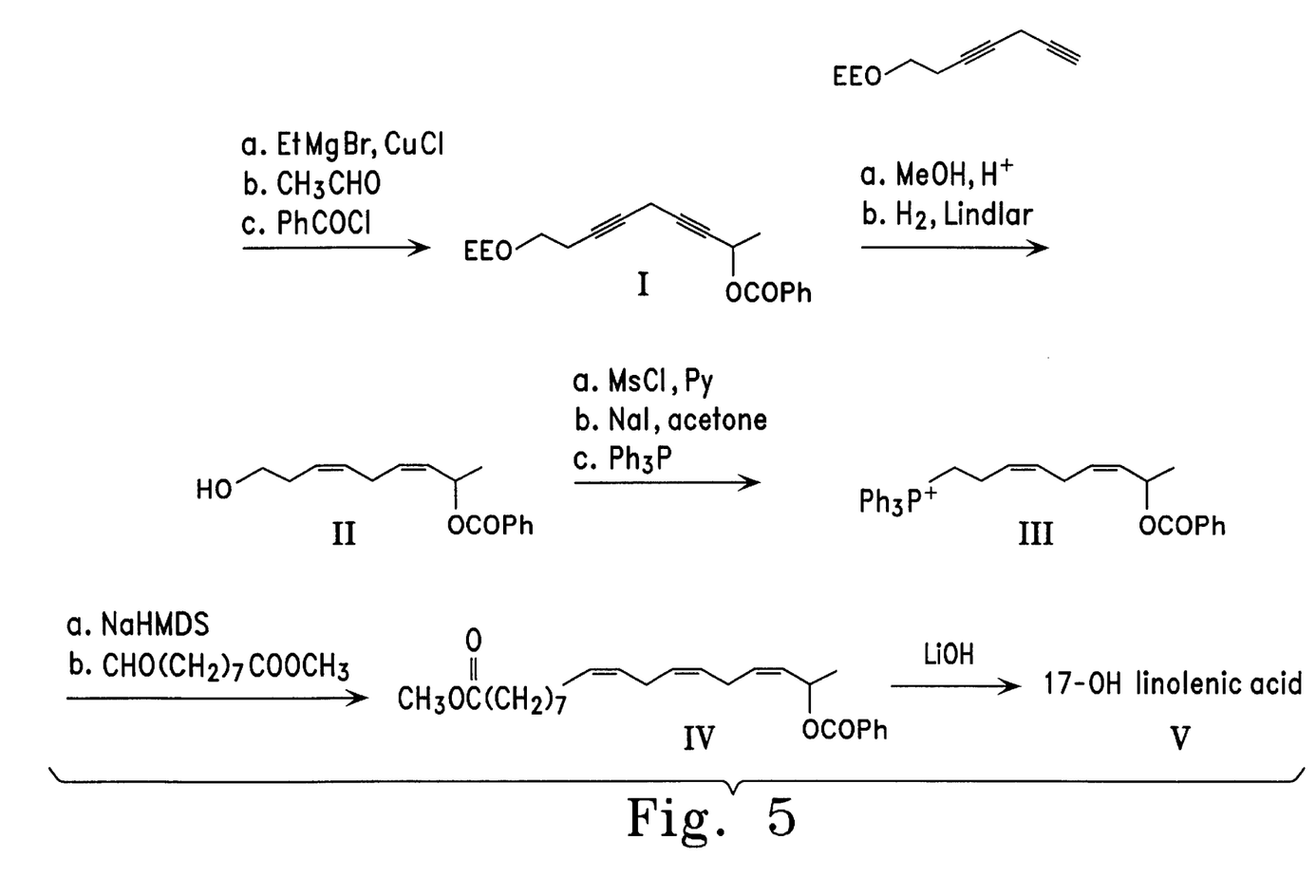
FIG. 5 shows the synthetic scheme for 17-hydroxylinolenic acid.

Racemic 17-hydroxylinolenic acid is synthesized, as illustrated in FIG. 5, as follows:

1-Ethoxyethyloxy-8-benzoyloxy-3,6-nonadiyne (1). A mixture containing approximately 2.3 g (about 12.8 mmol) of the ethoxyethyl ether of 3,6-heptadiynol (Huang, W., Pulaski, S. P., and Meinwald, J. *J. Org. Chem.*, Volume 48, 2270 1983; herein incorporated by reference in its entirety) in about 5 mL of tetrahydrofuran was cooled to about 0° C. and treated with about 13 mL of an approximately 1M solution of ethylmagnesiumbromide in tetrahydrofuran. After about 1 hour, the mixture was treated with approximately 1 mL of acetaldehyde and stirred for about 1 hour at approximately room temperature. The mixture was treated with approximately 1 mL of anhydrous pyridine followed by about 1.53 mL of benzoyl chloride and stirred for approximately an additional hour. The mixture was treated with about 10 mL of saturated ammonium chloride solution and about 15 mL of diethyl ether. The organic phase was separated, washed with brine, and dried over anhydrous MgSO$_4$. After filtration and removal of the solvent in vacuo, GC/MS analysis showed one major long retention time peak MS (rel. intensity) 327 (1, M–1), 255 (5), 115 (8), 105 (90), 91 (20), 77 (35), 73 (100), and 45 (93).

8-Benzoyloxy-Z,Z-3,6-nonadien-1-ol (II). A mixture of crude I in about 100 mL of methanol was treated with approximately 0.3 g of p-toluenesulfonic acid. After about 3 hours TLC analysis indicated almost no starting material remained. GC/MS analysis showed one long retention time component (>95%) MS (rel. intensity) 256 (0.5, M+), 255 (3), 226 (1), 134 (5), 133 (2), 105 (100), 91 (12), 77 (35), and 51 (20). This mixture was treated with about 5 mL of saturated NaHCO$_3$, and the solvent was removed in vacuo. The residue was taken up in ether and purified through a short silica gel (hexane/ ether approximately 9:1) column to provide approximately 2.7 g of unstable 3,6-nonadiyn-1,8-diol, 8-benzoate. A mixture of approximately 1.25 g of this material in about 60 mL of ethanol containing approximately 0.32 g of quinoline and approximately 180 mg of lindlar catalyst was hydrogenated at atmospheric pressure until hydrogen uptake ceased. After about 2 hours, approximately 100 mg of additional catalyst was added and the reaction was continued until hydrogen uptake ceased (Mori, K, and Ebata, T., *Tetrahedron,* Volume 42, 3471, 1986; herein incorporated by reference in its entirety). GC/MS analysis showed one major long retention time component: MS (rel. intensity) 260 ( 1, M+), 229 (1), 138 (15), 123 (2), 105 (100), 93 (18), 91 (15), 79 (45), and 77 (50). The product was isolated by filtration through celite and removal of the solvent in vacuo. The residue was taken up in ether, washed with dilute HCl, and brine, and dried over $MgSO_4$. The infrared spectrum of a sample of this material isolated by preparative gas chromatography showed important absorptions at 3433 (br), 3053, 3012, 1712, 1602, 1580, 1450, 1268, 1108, 1043, and 709cm$^{-1}$.

1-Triphenylphosphonium-8-benzoyloxy-Z,Z-3,6-nonadiene, iodide (III). A mixture containing approximately 2.025 g (approximately 7.8 mmol) of II in about 50 mL of methylene chloride was treated at about 0° C. with about 1.6 mL of triethyl amine and about 0.75 mL of methanesulfonylchloride, the mixture was stirred about two hours, washed with an approximately saturated Na $HCO_3$ solution and dried over $MgSO_4$. GC/MS analysis showed the presence of a single product, GC/MS (rel intensity) 243 (2, M-$CH_3SO_3$), 233 (2, M-$C_6H_5CO$), 175 (5), 120 (20), 105 (100), 91 (15), 79 (18), 77 (35). After the solvent was removed in vacuo, the residue was taken up in about 50 mL of acetone and stirred with approximately 1.35 g of NaI for about 2.5 hours. The solvent was removed in vacuo, the residue was taken up in ether and washed with about 10% $Na_2S_2O_3$, brine, dried over anhydrous $MgSO_4$ and the solvent removed in vacuo. GC/MS analysis showed one major component (>95%) MS (rel. intensity) 248 (5, M+–122), 175 (8), 121(12), 105(100), 93(25), 79(20), and 77(45). The residue was taken up in about 7 mL of acetonitrile and treated with approximately 2.0 g of triphenylphosphine and heated to reflux overnight. Removal of the solvent provided an unstable, hygroscopic brittle foam, insoluble in anhydrous ether or benzene.

Methyl, 17-benzoyloxylinolenate (IV). A mixture containing approximately 0.65 g of the powdered brittle foam in about 15 mL of tetrahydrofuran was cooled to approximately –80° C. under an argon atmosphere, and treated with about 1.0 mL of an approximately 1M commercial solution of sodium hexamethyldisilazide (3. Bestmann, H. J., Roth, K., Michaelis, K., Vostrowsky, O., Schafer, H. J., and Michaelis, R., *Liebigs Ann. Chem.,* 417, 1987; herein incorporated by reference in its entirety). After about 15 minutes, a solution containing approximately 0.2 g (1 mmol) of methyl-9-oxononanoate (Pennington, F. C., Clemer, W. D., McLamore, W. M., Bogert, V. V., and Solomons, I. A., *J. Am. Chem. Soc.,* Volume 75, 109, 1953; Burgstahler, A. W., Weigel, L. O., and Shaefer, C. G. *Synthesis,* 767, 1976; both incorporated by reference in their entirety) in about 2 mL of tetrahydrofuran was added and the mixture was stirred overnight and warmed to approximately room temperature. After the addition of approximately 15 mL of saturated ammonium chloride solution and approximately 15 mL of ether, the organic phase was separated, dried over $MgSO_4$, and the solvent was removed in vacuo to provide approximately 0.4 g of a mixture. GC/MS analysis revealed the presence of the starting oxo-ester, triphenylphosphine oxide, and a single very long retention time peak (20)%: MS (rel intensity) 290 (5, M–122), 147 (3), 133 (10), 119 (12), 105 (100), 94 (20), 93 (15), 87 (5), 81 (15), 79 (25), 78 (27), 77 (30), 74 (5), and 55 (20).

17-Hydroxylinolenic acid (V). The above mixture was stirred with aqueous LiOH, approximately 0.5 M, and tetrahydrofuran at about room temperature for about 8 hours. After removal of the solvent in vacuo, the solution was extracted with ether, acidified with dilute HCl, and extracted a second time with ether ( about 20 mL). The second ether extract was dried over $MgSO_4$, filtered, and the solvent removed in vacuo to provide approximately 0.12 g of residue. GC/MS analysis revealed the major component which had a mass spectrum MS (rel intensity) 276 (5, M–18), 221 (2), 193 (1), 147 (5), 133 (10), 119 (12), 107 (13), 105 (15), 95 (10), 94 (15), 93 (13), 91 (25), 84 (20), 81 (20), 80 (30), 79 (33), 69 (20), 67 (27), 60 (15), 55 (70), 43 (100), and 41 (80).

The 17-hydroxylinolenic acid is then coupled to glutamine as follows:

Approximately 1.1–1.2 equivalents of glutamine (D- or L-) was exchanged into its lithium salt on an approximate 5 cm×1 cm ID column packed with Amberlite CG-50 (100–200 mesh, Sigma, St. Louis, Mo.), cation exchange resin following the procedures described by R. Kramell et al, *Tetrahedron,* Volume 44, 5791, 1988; herein incorporated by reference in its entirety. The product was dispersed in about 1 to 2 ml of DMF (Dimethyl formamide). About one to two hundred microliters of water was added followed by about 1.1–1.2 equivalents of freshly distilled triethylamine. In a second container, approximately 1 equivalent (approximately 10–50 mg) of 17-hydroxylinolenic acid was dissolved in approximately 2 ml of DMF followed by approximately 1.1–1.2 equivalents of HOBT (Hydroxybenzotriazole). To this solution, approximately 1.1–1.2 equivalents of EDAC (1-Ethyl-3 (Dimethylaminopropyl)carbodiimide) was added and the solution stirred for about 1 minute before the contents of the first container was added to the second and the mixture stirred overnight at about room temperature. Following the coupling reaction, about 4 ml of water was added and the acidity adjusted to about pH 3 with approximately 1 M HCl. The mixture was extracted approximately 3 times with distilled water. The organic phase was concentrated to near dryness and the residue was redissolved in about 2 ml of methylene chloride. The methylene chloride fraction was in aliquots of about 0.2 ml put on an activated 3 ml 10SPE diol cartridge (Bakerbond, J. T. Baker, Phillipsburg, N.J.). The column was rinsed with a first fraction of about 3 ml methylene chloride followed by approximately 2 ml of methanol. The methanol fraction was finally purified on HPLC using an LDC 4100 pump with SM5000 diode array UV detector (LDC Analytical, Riviera Beach, Fla.), monitoring UV detection from about 190 to 360 nm. The reverse phase column (YMC 18 ODS-AQ S-5 200 Å, 46 mm ID×250 mm YMC CO., ltd., Kyoto, Japan) was eluted with a solvent consisting of 25% acetonitrile in water with 0.4 mM ammonium acetate (Aldrich), using a flow of about 1.2 ml/min. The synthetic product had a retention time of approximately 26 minutes, which was identical to that of the natural product. The synthetic conjugates also show identical UV absorption. FAB-MS/MS analysis gives a daughter ion spectrum identical to that of the natural product. GC/MS analysis of the methylated synthetic hydroxy acid show this to be identical to the methyl ester of the hydroxy acid obtained by methanolysis of the natural product.

EXAMPLE 6

Figure 6:
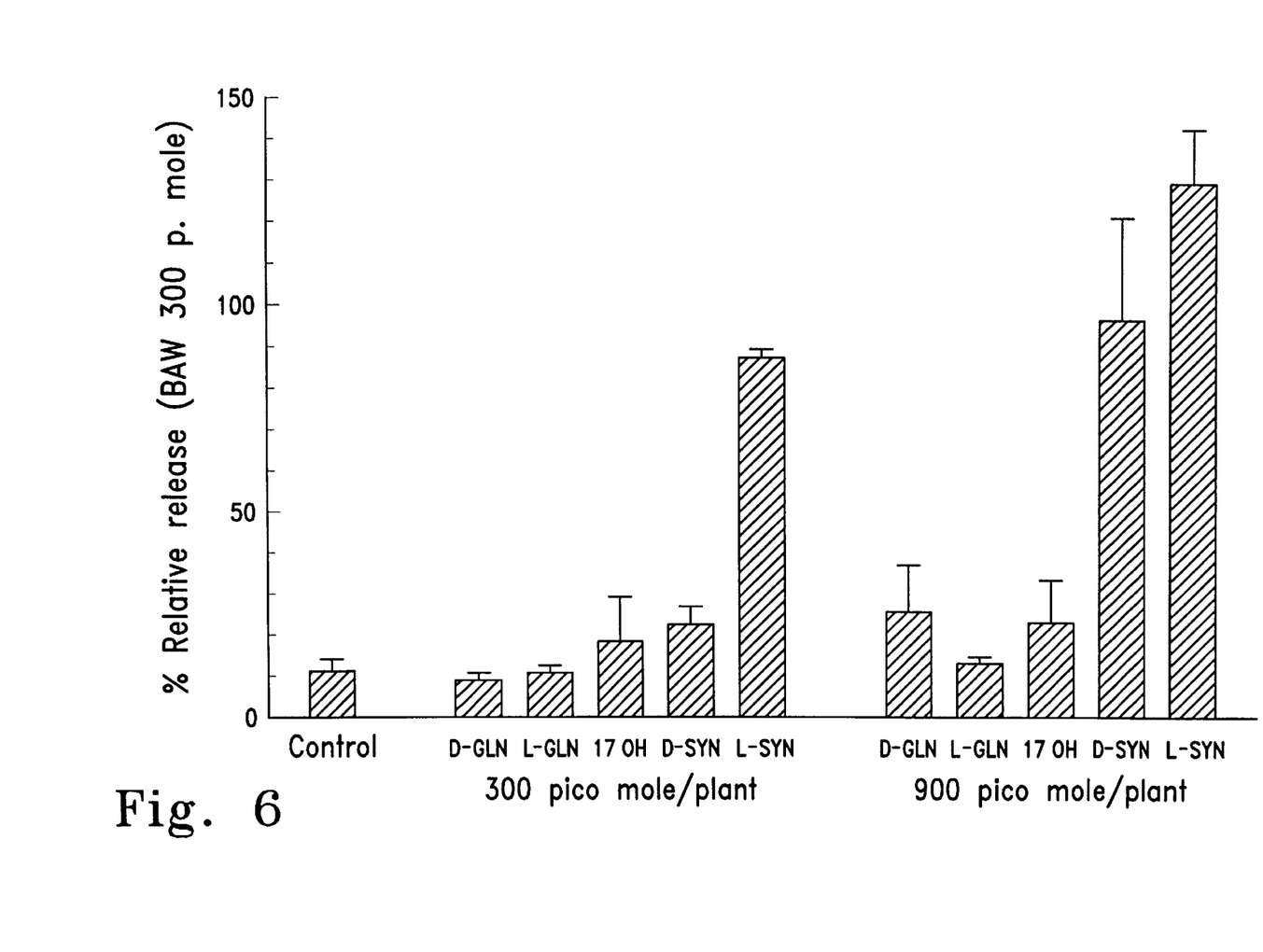
Figure 7:
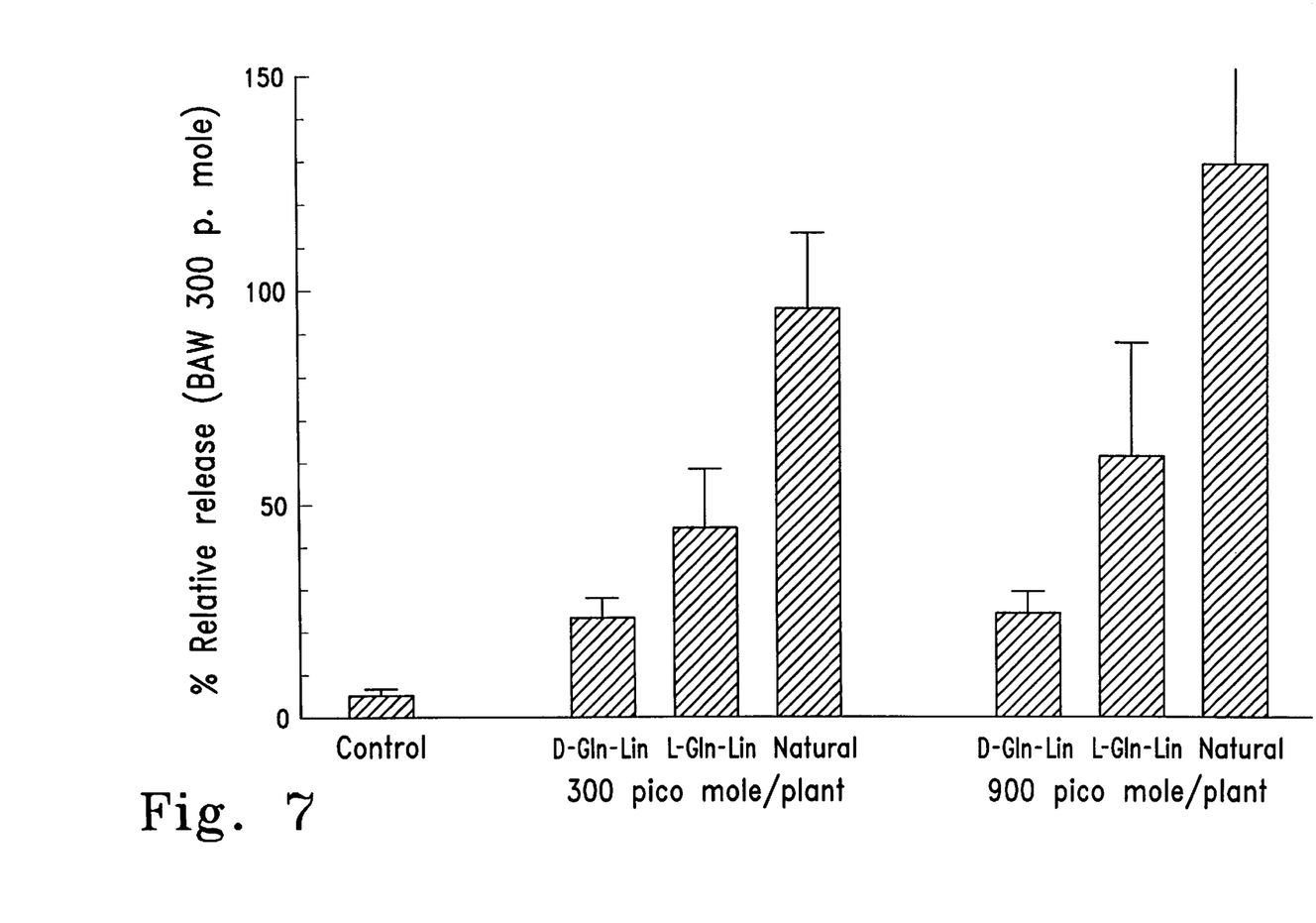
FIG. 7 is a graph showing average of three replicates of relative release of volatiles collected under 2 hours form three corn seedlings that had been treated with 15 microliters of regurgitate equivalents/seedling (300 picomoles/plant) or 45 microliters of regurgitate equivalent/seedling (900 picomoles/seedling) of, L-glutamine derivative of linolenic acid (L-Gln-Lin), the D-glutamine derivative of linolenic acid (D-Gln-Lin), natural elicitor (Natural), and just buffer (Control). The combined amount in nanogram of Caryophyllene, alpha-trans-gergamotene, (E)-beta-farnesene, (E)-nerolidol, and (3E,7E)-4, 8, 12-trimethyl-1, 3, 7, 11, tridecatetraene was used to calculate the release relative to that of corn seedlings treated with 15 microliter regurgitate (300 picomole/seedling of natural elicitor).
Figure 8:
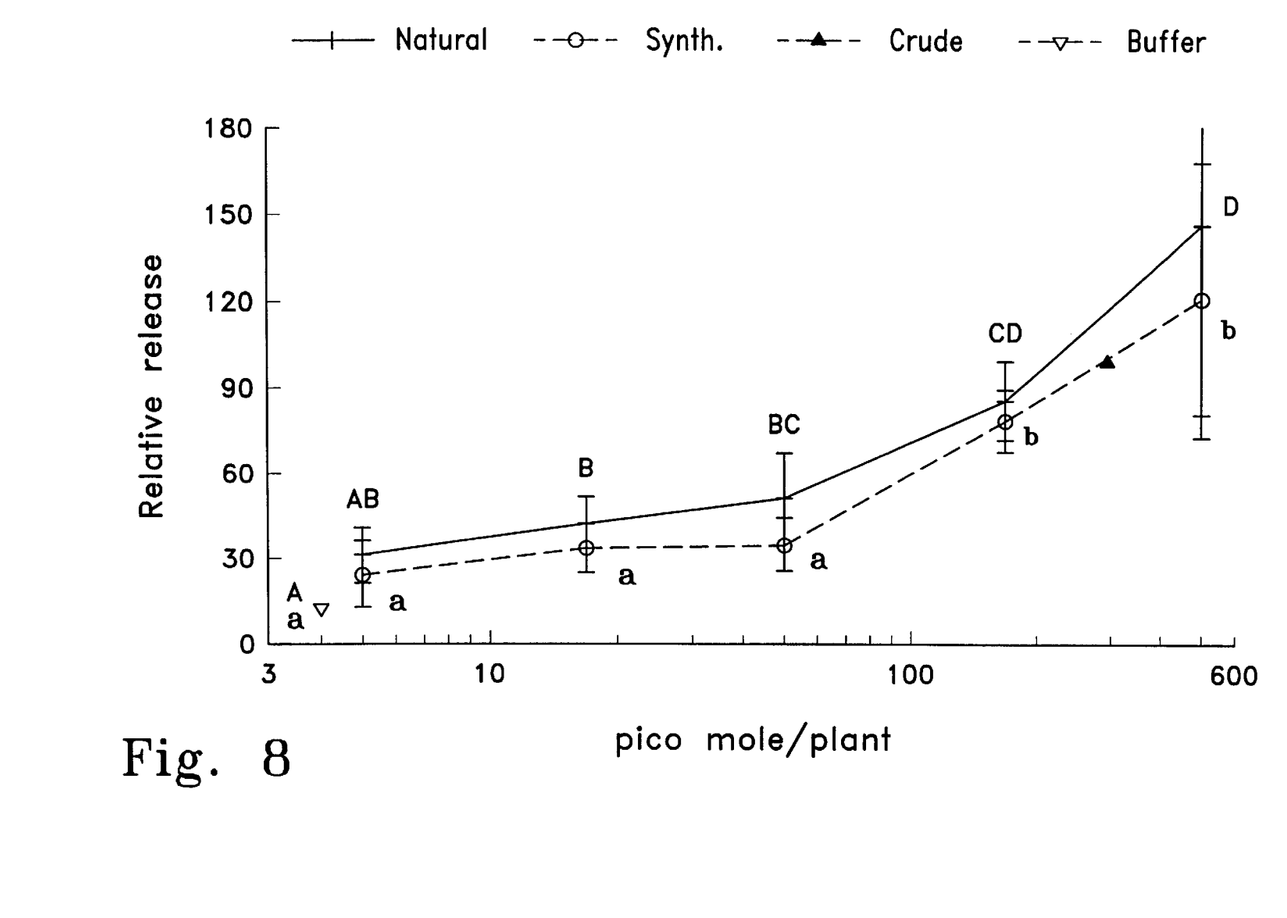

The synthetic compounds are bioassayed with excised corn seedlings as described above in Example 1. Approximately 300 pmol (approximately 135 ng) and approximately 900 pmol (approximately 405 ng) of pure synthetic D-Gln and L-Gln forms of the active compound, purified natural product, sodium salts of synthetic 17-hydroxylinolenic acid, D-glutamine, L-glutamine were tested. The results are shown in FIG. 6. The synthetic L-glutamine form is as active as the natural product. The D-glutamine form shows activity at the higher dose. Neither the free hydroxy acid or D- or L-glutamine alone show any biological activity. Approximately 300 pmol (approximately 135 ng) and approximately 900 pmol (approximately 405 ng) of pure synthetic D-Gln and L-Gln forms of linolenic acid and purified natural product were tested. The results are shown in FIG. 7. The L-glutamine form of linolenic acid showed more biological activity than the D-glutamine form, and the biological activity at either dose was approximately half of that of the natural product. Bioassaying at approximately 5, 17, 50, 170 and 500 pmol/plant of natural elicitor and the synthetic N-(17-hydroxylinolenoyl-L-glutamine, shows almost identical dose response curves. The results are shown in FIG. 8. Therefore, it can be concluded that the most biologically active compound identified so far is N (17-hydroxy 9, 12, 15 octadecatrienoyl)-L-glutamine.

The foregoing detailed description is for the purpose of illustration. Such detail is solely for that purpose and those skilled in the art can make variations therein without departing from the spirit and scope of the invention.

We claim:

1. A composition for inducing plants to produce and/or release insect attractant volatiles, said composition comprising:

an effective amount of a compound selected from the group consisting of N-(17-hydroxylinolenoyl)-L-glutamine, N-(linolenoyl)-L-glutamine, and mixtures thereof, to induce plants to produce and/or release insect attractant volatiles; and a surfactant.

2. The composition of claim 1, wherein said compound is N-(17-hydroxylinolenoyl)-L-glutamine.

* * * * *